United States Patent [19]

Olinger et al.

[11] 4,008,711
[45] Feb. 22, 1977

[54] METHOD AND APPARATUS FOR NON-INVASIVE DETECTION OF INTRACRANIAL ANEURYSMS

[75] Inventors: Charles P. Olinger; Jacob F. Wasserman, both of Cincinnati, Ohio

[73] Assignee: Charles P. Olinger, Cincinnati, Ohio

[22] Filed: June 30, 1975

[21] Appl. No.: 591,332

[52] U.S. Cl. .......................... 128/2 K; 128/2.05 S; 179/1 ST

[51] Int. Cl.[2] ........................................... A61B 7/04

[58] Field of Search ...................... 128/2 K, 2.05 S; 179/1 ST

[56] References Cited

UNITED STATES PATENTS

| | | | |
|---|---|---|---|
| 2,648,822 | 8/1953 | Walter | 324/77 |
| 2,676,512 | 4/1954 | Krasno | 128/2 X |
| 3,052,756 | 9/1962 | Seven et al. | 128/2.05 S |
| 3,171,892 | 3/1965 | Pantle | 179/1 ST |
| 3,181,528 | 5/1965 | Brackin | 128/2 K |
| 3,188,645 | 6/1965 | Trumpy et al. | 128/2.05 S X |
| 3,525,810 | 8/1970 | Adler | 128/2.05 S X |
| 3,777,740 | 12/1973 | Hokanson | 128/2 V |
| 3,799,147 | 3/1974 | Adolph et al. | 128/2.05 S |
| 3,878,832 | 4/1975 | Tickner et al. | 128/2.05 S |

OTHER PUBLICATIONS

Richardson, C. et al., Trans Amer. Neurological Assoc., 1951, pp. 151–154.

Simkins, T. E. et al., Letters in Applied & Engng. Sciences, vol. 1, pp. 85–100, 1973.
Ferguson, G. G., Journ. of Neurosurgery, vol. 33, pp. 485–497, 1970, & vol. 37, pp. 666–677, 1972.
Allen, N., et al., Medicine, pp. 227–247, 1962.
Locksley, H. B., Report–on Cooperative Study of Intracranial Aneurysm and Subarachnoid Hermorr., Sec. V, Part 1, 219, Nat. Inst. of Neur. Diseases and Blindness – U.S. Pub. Health Service.
Jain, K. K., Surgery, pp. 347–350, Aug. 1963.
Bruns, D. L., Amer. Journ. of Medicine, vol. 27, pp. 360–374, 1959.

Primary Examiner—Kyle L. Howell
Attorney, Agent, or Firm—Wood, Herron & Evans

[57] ABSTRACT

Intracranial aneurysms generate aneurysm-characteristic sounds which emanate externally from the head, are monitored, and are then analyzed to produce information indicative of the probable existence of the aneurysm. The method is non-invasive, does not require hospitalization, and is repeatedly used to diagnose probable aneurysm presence and the onset and continuation of spasm. Information from repeated samplings aids in following and diagnosing patient status pre-bleed, during bleed, post-bleed and pre- and post-operative.

26 Claims, 33 Drawing Figures

TIME HISTORY — PURE TONE

POWER SPECTRUM — PURE TONE

TIME HISTORY — NOISE

POWER SPECTRUM — NOISE

TIME HISTORY — NOISE & PURE TONE

POWER SPECTRUM — NOISE & PURE TONE

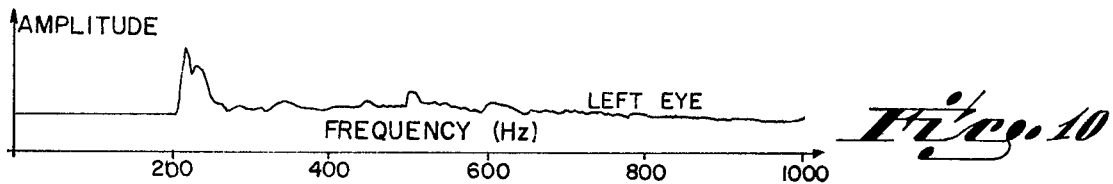
Fig. 10
Fig. 10a
NORMAL
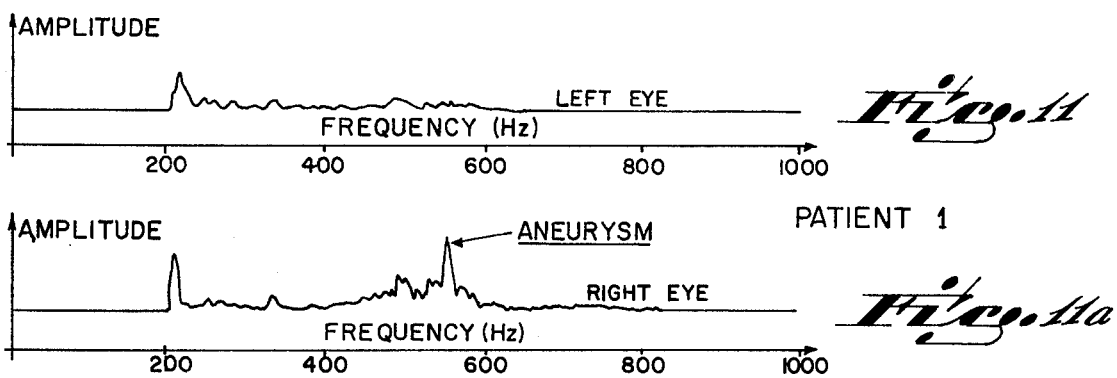
PATIENT 1
Fig. 11
Fig. 11a
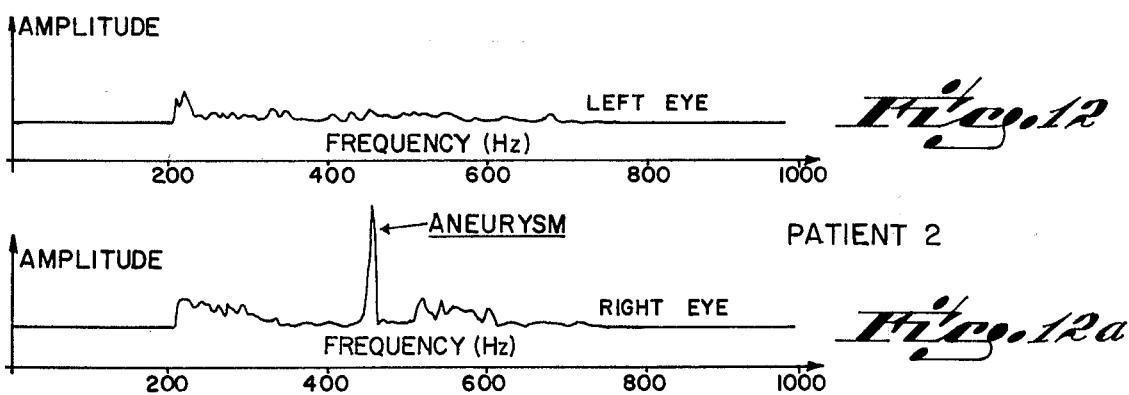
PATIENT 2
Fig. 12
Fig. 12a
1st TEST, PRE-OPERATIVE
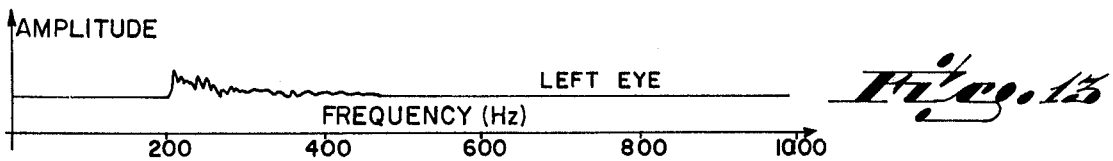
Fig. 13
PATIENT 2
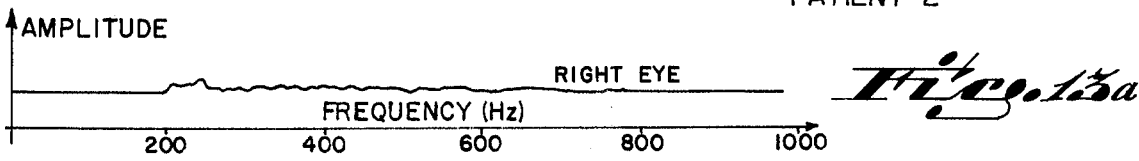
Fig. 13a
2nd TEST, POST-OPERATIVE

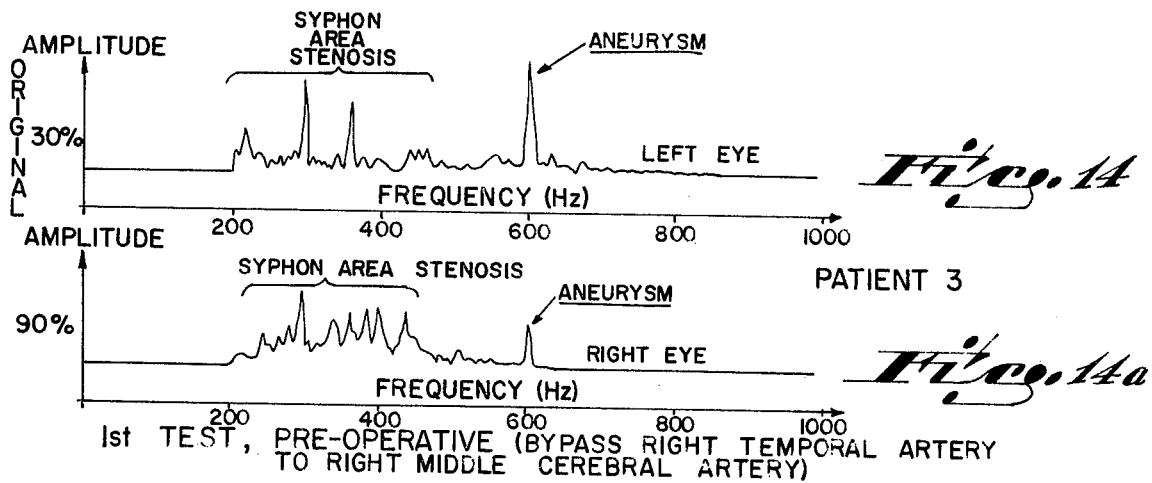
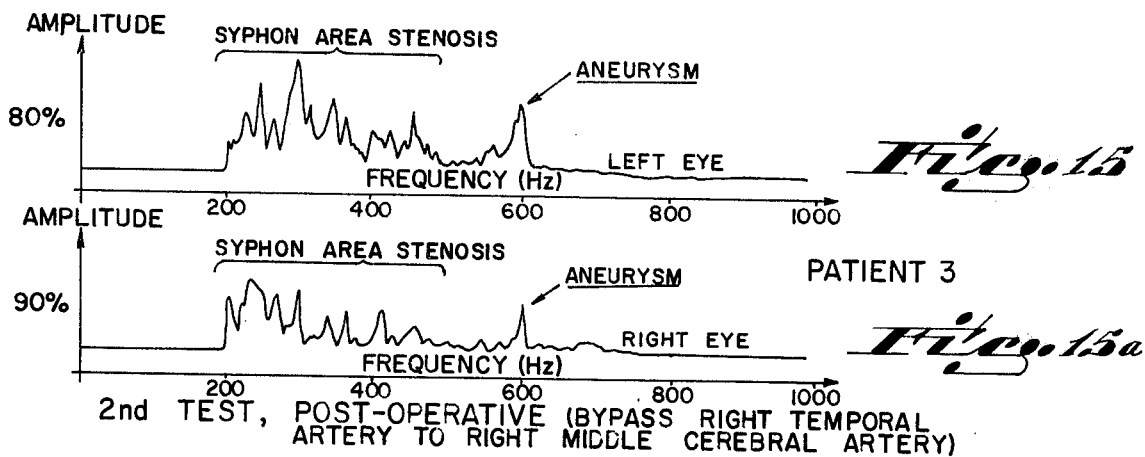
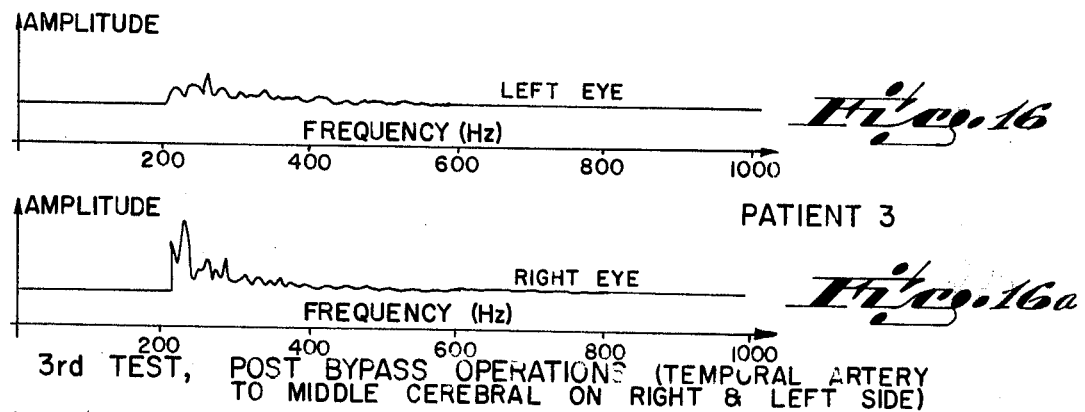
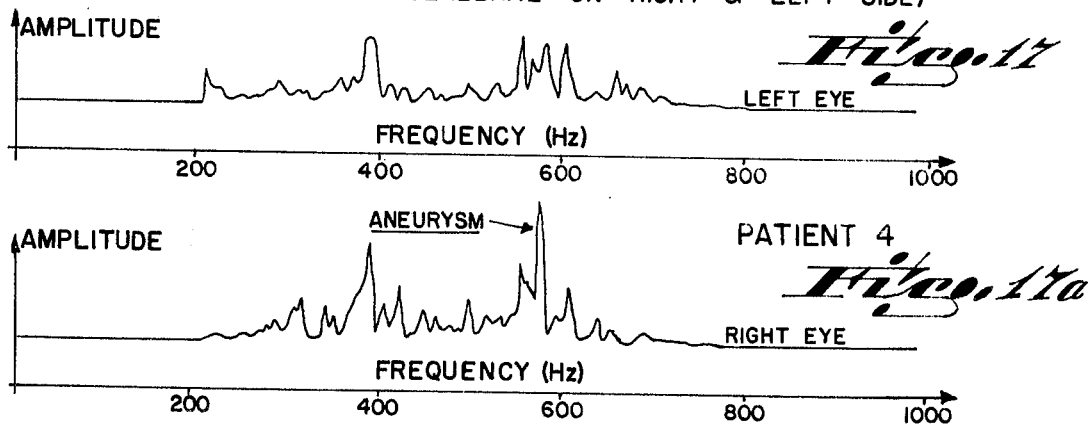

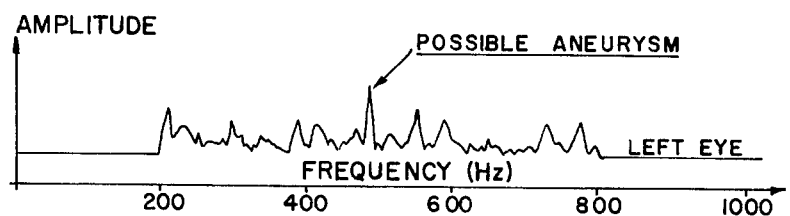
Fig. 18
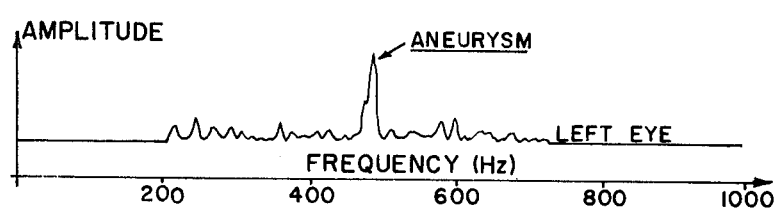
Fig. 18a
PATIENT 5
TWO DAYS POST BLEED
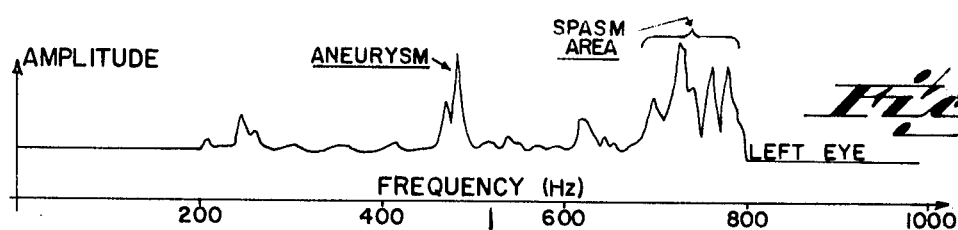
Fig. 19
Fig. 19a
PATIENT 5
SEVEN DAYS POST BLEED
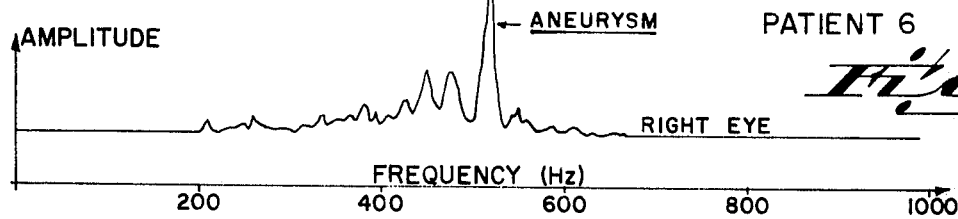
Fig. 20
Fig. 20a
PATIENT 6
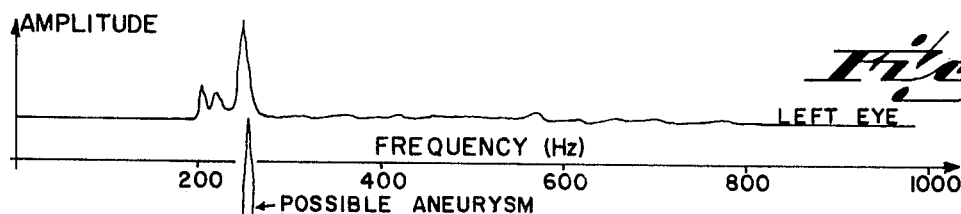
Fig. 21
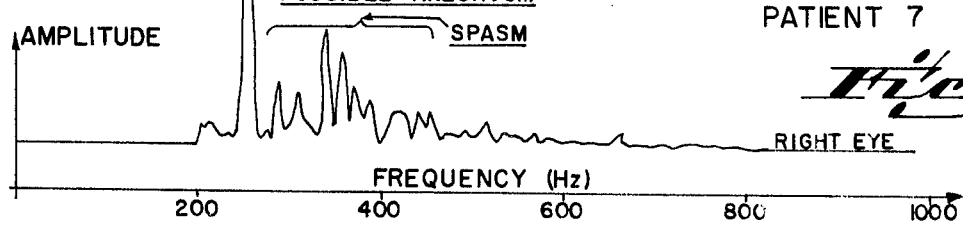
Fig. 21a
PATIENT 7

METHOD AND APPARATUS FOR NON-INVASIVE DETECTION OF INTRACRANIAL ANEURYSMS

This invention relates to methods for detecting aneurysms and particularly to methods for detecting the probable existence of cerebral aneurysms and for diagnosing and following cerebral vascular spasm in humans.

Intracranial aneurysms present a serious clinical problem since their rupture, in a majority of affected patients, causes either death or permanent brain damage. This prognosis is even more critically serious for patients with aneurysms of the anterior communicating artery, most of whom die even before they can reach the hospital. The problem is particularly frustrating since it is known that half of the patients with intracranial aneurysms develop warning symptoms before rupture — in many cases, sudden onset of headache or dizziness.

If the family physician or emergency room staff could recognize the warning symptoms and easily detect probable aneurysm presence, surgeons could then see the patient before any neurological deficit and while they are in a condition ideally suited for surgery.

Since no reliable non-invasive technique is available, however, angiography is presently the only method available for diagnosing aneurysm. This entails expensive hospitalization, trauma and patient risk, and therefore is not suited for investigating vague, prodromal symptoms even through these symptoms might precede fatal aneurysm rupture.

Intracranial aneurysms are not uncommon, and have been found in as many as one in 200 autopsies, though a small proportion of these may have produced serious symptoms. Patients with high blood pressure, in the age group 40–60, with polycystic kidney, and with coarctation of aorta and migraine exhibit a higher incidence of aneurysm. The aneurysm problem is thus pertinent in a significant percentage of patients.

Since, however, angiography is the only method available for diagnosing aneurysm, a physician confronted with possible aneurysm warning signs must judge whether the symptoms warrant the trauma, and expense, of an angiogram; the patient's headache, dizziness, or nausea may not be serious enough to provide convincing evidence that angiography should be performed.

If a physician can be reasonably certain of an aneurysm's presence before its rupture, successful surgical techniques (including clipping, inducing clots in the aneurysm, and wrapping the aneurysm in plastic) can be used while the patient is in optimal condition. After rupture, when the aneurysm's presence is only too apparent, the patient's chances of recovery to a condition in which surgery can be performed become much less.

A correlated difficulty in diagnosing and treating aneurysm cases is that of "bleeds" (small leaking from aneurysms) and resultant spasm. Such bleeding from aneurysms can be detected by examining the cerebral-spinal fluid for the presence of blood. Typically, spasm occurs approximately three or four days after an aneurysm bleed, and extends for one or two weeks thereafter. During spasm, the performance of angiography or of surgical corrective procedures is contra-indicated due to high patient risk. When post-bleed spasm ceases, however, angiography and surgical procedures can be performed to diagnose and rectify the aneurysm problem.

It is thus desirable to diagnose the onset and follow the existence of spasm and to be able to detect its cessation; but angiography does not provide a suitable technique for performing such functions due to its expensive and traumatic nature.

Accordingly, it has been one objective of the present invention to provide a method for non-invasively detecting the probable existence of a cerebral aneurysm in humans.

A further objective of the invention has been to provide a method for non-invasively diagnosing and following spasm in humans.

A still further objective of the invention has been to provide an inexpensive, non-invasive apparatus and method useful for externally and repeatedly diagnosing cerebral aneurysms and spasm.

To these ends, a preferred embodiment of the invention provides a method by which the probable existence of cerebral aneurysms can be non-invasively detected. The method of includes monitoring sound waves emanating from predetermined external areas of the head, and analyzing the signals produced by the sound waves to determine the existence of an aneurysm-characteristic sound.

While it is known that aneurysms exposed during open surgery tend to vibrate during a constant frequency, this knowledge has heretofore been useless. We have found that cerebral aneurysms normally generate an aneurysm-characteristic sound wave of a constant frequency in the approximate range of from 200 to 800 Hz. and that these sound waves are detectable not only at the surface of the aneurysm but externally of the head via transmission through the cerebral spinal fluid to the eye and the closed eye lid. By monitoring sound waves emanating from the eye, and by analyzing the waves to distinguish the aneurysm-characteristic sound from other sounds, the probable existence of an aneurysm can be diagnosed. Moreover, we have discovered that effective, non-invasive analysis of aneurysm-characteristic sounds is enhanced by analyzing sound emanating from the head at the moment of peak arterial pulse pressure in the cerebral vascular system.

In a preferred embodiment of the invention, sound waves emanating from the patient's eyes are non-invasively monitored and converted by an electronic microphone into electrical signals which are filtered, amplified, filtered again and recorded on one channel of a magnetic tape. A heart signal, to be utilized as a computer trigger signal, is filtered and recorded on another channel of the tape. The signals are then passed through a final filter to a computer having a Fourier analysis capability. Data recorded over the patient's eyes is sampled by the computer at peak pulse pressure in the cerebral vascular system and the result of the computer analysis is displayed in the form of a spectrum on a cathode-ray tube and is plotted to provide a permanent record. The displayed spectrum is considered to indicate the probable existence of an aneurysm if it includes a relatively high energy peak in the range of 200 Hz. to 800 Hz. and having an amplitude one and one-half times greater than the amplitude of any adjacent peak within 50 Hz. frequency of the high energy peak.

The invention is also used to diagnose and trace post-bleed spasm which appears in the spectrum as a wide band frequency display. This diagnosis is used to determine the existence of spasm and to determine optimum times for performing angiography or surgery.

These and other objectives and advantages of the invention will become readily apparent from the following detailed description of a preferred embodiment of the invention and from the drawings in which:

FIG. 10 and 10a are plots of the frequency spectrum of sounds monitored over the respective left and right eyes of a normal patient;

FIGS. 11 and 11a are plots of the frequency spectrum of sounds monitored over the respective left and right eyes of Patient No. 1;

FIGS. 12 and 12a are plots of the frequency spectrum of sounds pre-operatively monitored over the respective left and right eyes of Patient No. 2;

FIGS. 13 and 13a are plots of the frequency spectrum of sounds post-operatively monitored over the respective left and right eyes of Patient No. 2;

FIGS. 14 and 14a are plots of the frequency spectrum of sounds pre-operatively monitored over the respective left and right eyes of Patient No. 3;

FIGS. 15 and 15a are plots of the frequency spectrum of sounds post-operatively monitored over the respective left and right eyes of Patient No. 3;

FIGS. 16 and 16a are plots of the frequency spectrum of sounds monitored over the respective left and right eyes of Patient No. 3 subsequent to a second operation;

FIGS. 17 and 17a are plots of the frequency spectrum of sounds monitored over respective left and right eyes of Patient No. 4;

FIGS. 18 and 18a are plots of the frequency spectrum of sounds monitored over the respective left and right eyes of Patient No. 5, about two days post-bleed;

FIGS. 19 and 19a are plots of the frequency spectrum of sounds monitored over the respective left and right eyes of Patient No. 5 about 7 days post-bleed;

FIGS. 20 and 20a are plots of the frequency spectrum of sounds monitored over the respective left and right eyes of Patient No. 6;

FIGS. 21 and 21a are plots of the frequency spectrum of sounds monitored over the respective left and right eyes of Patient No. 7.

Figure 1:
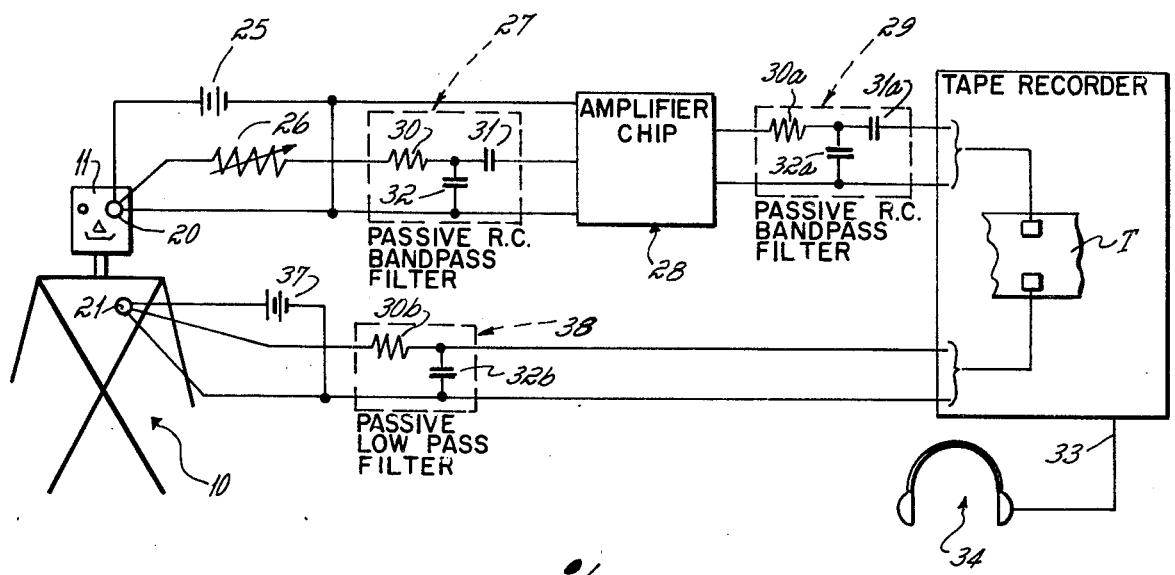
FIG. 1 is a diagrammatic illustration of the sound monitoring and recording portion of the invention.

Prior to specifically describing the invention in detail, it is believed that a brief resume of cerebral aneurysms and their corresponding problems would be helpful to a clear understanding of the invention. A cerebral aneurysm typically takes the form of a blood-filled berry or sac-like structure located on an artery wall somewhere on the Circle of Willis, a communicating series of arteries located in the human head approximately at eye level and in the intracranial region behind the eyes. Such cerebral aneurysm may form on the posterior communicating arteries or on the anterior cerebral arteries of the Circle of Willis; most commonly at the points where the arteries branch or diverge. Once an aneurysm has formed, it may simply continue to exist for some time and, if none of the recognized symptoms occur, the aneurysm would normally go undetected until it bled, i.e., leaked slightly into the surrounding spinal fluid, or ruptured, an occurrence usually resulting in death or permanent brain damage.

If an aneurysm leaks or "bleeds" short of a massive rupture, the surrounding arteries tend to contract in a phenomenon known as spasm. This is simply the natural reaction of arteries to close off the leak. Eventually, the leaking area of the aneurysm may clot and the leak will at least be temporarily stopped.

The onset of spasm usually occurs approximately three or four days after a bleed and lasts for approximately one week to two weeks after onset. During this time, utilization of surgical techniques to rectify the aneurysm problem, or the use of angiography techniques to diagnose the problem are very dangerous as they involve an extremely high risk to the patient. It is thus important not only to detect an aneurysm prior to rupture or bleed, but it is further important to be able to periodically diagnose the condition of the patient during spasm in order to determine the appropriate times during which angiography or surgical techniques can be utilized with minimal risk to the patient.

The ability to effectively diagnose the probable existence of an aneurysm by an inexpensive, non-invasive, no-risk technique which is easily repeatable is thus highly desirable but has not been available prior to this invention.

DESCRIPTION OF A PREFERRED EMBODIMENT

The present invention is based on the concept that an aneurysm produces an aneurysm-characteristic sound which can be non-invasively monitored and analyzed to distinguish it from other body sounds. The method of the preferred embodiment includes detecting the probable existence of cerebral aneurysms by non-invasively monitoring body sounds over predetermined areas of the head and analyzing the sounds to indicate the probable existence of an aneurysm-characteristic sound. The invention further contemplates a method by which spasm produced sound resulting from an aneurysm bleed can be detected, followed non-invasively without the risk of current angiography techniques, and distinguished from other sound-producing disease such as atherosclerosis (stenosis for example).

More particularly, the invention is predicated upon the discovery that intracranial aneurysms generate an aneurysmcharacteristic sound comprising a constant frequency in the range of 200 Hz. to 800 Hz. which emanates from the head, can be monitored on external portions of the head, and can thereafter be analyzed to produce a positive indication that the aneurysm-characteristic sound is present, thereby indicating the probable existence of an aneurysm. To enhance detection, sounds emanating from the head are monitored during peak cerebral arterial pulse pressure in the cerebral vascular system. For the purposes of description, an aneurysm-characteristic sound shall be defined as a constant frequency sound wave in the range of 200 to 800 Hz. emanating from the head and having an amplitude about one and one-half times as great as other sounds emanating from the head within a frequency range of 50 Hz. of the aneurysm characteristic sound wave. Of course, the detection of any constant frequency sound wave within 200 to 800 Hz. should be inspected carefully as skilled physicians will appreciate.

DESCRIPTION OF PREFERRED APPARATUS AND OPERATION

Turning to the drawings, the invention will be further understood by now describing the method and apparatus by which body sound waves emanating from the head are non-invasively monitored, converted to electrical signals, and thereafter analyzed in order to determine the probable existence of an intracranial aneurysm. Referring specifically to FIG. 1, a patient diagrammatically indicated at 10 is placed in a supine position during which time various body sounds are monitored and recorded. While these sounds may be monitored at various predetermined locations on the patients head 11, FIG. 1 depicts the monitoring of sound waves emanating from the patient's eye lid by means of the microphone 20. The microphone 20 is an electronic, low-noise microphone sold by the Thermo-Electron Corporation of Waltham, Massachusetts under the designation Model No. 5336-C. This microphone has a frequency response of approximately 50 to 16,000 Hz.; a sensitivity of 59 dBV ±dB (re: 1V/ubar); a noise level of approximately 26 dB SPL; an output impedance of about 1,700 ohms (±700); and a distortion (3% THD) of about 139 dB SPL. This microphone is enclosed in an acoustical chamber for isolating environmental noise as will be more specifically hereinafter described.

The sound waves monitored by the microphone are converted into an electrical signal which is thereafter filtered, amplified, filtered again and then recorded on one channel of a magnetic tape T. The heartbeat of the patient 10 is monitored, as by a microphone 21, to provide a trigger signal corresponding to contraction of the left ventrical of the heart pumping blood throughout the body. The sound of the heartbeat is converted into an electronic signal which is filtered through a passive, low pass filter and is thereafter recorded on a second channel of the magnetic tape T.

Referring specifically to the filtering and amplifying circuitry shown in FIG. 1, the circuit includes a 27-volt source of electricity such as a battery 25, a 5,000 ohm variable resistor 26, (used to vary the signal strength when desired), a passive RC band/pass filter 27, an amplifier chip 28, a second passive RC band/pass filter 29.

The RC band/pass filters 27 and 29 are alike and comprise three low-noise components. In filter 27 these are a 3,900 ohm resistor 30, a 0.033 microfarad capcitor 31, and a .1 microfarad capacitor 32. Similar elements of the second filter 29 are designated by similar numbers followed by the suffix "a". As will be appreciated, each of these filters "windows" or passes electrical signals having a frequency between 150 and 2,000 Hz.

The amplifier chip 28 is a standard item of commerce and is manufactured as a pre-amp chip by the Motorola Company under its Model designation No. MC 1741 cp. The amplifier chip 28 receives the filtered signal from the filter 27 and boosts the signal gain by a factor of approximately 1,000, such gain made possible by the filtering of the input signal to a relatively small range, i.e., between 150 to 2,000 Hz.

Thereafter the amplified signal is connected to the second filter 29, also constructed to pass only those signals in the range of 150 to 2,000 Hz., and is recorded on one channel of tape T.

One tape recorder found to be suitable is the two-track magnetic tape recorder manufactured by the Sony Corporation under its model designation 152-SD. The recorder includes a monitoring output 33 which may be connected to an earphone set 34 for use by the system operator in order to monitor the sound being recorded on the magnetic tape T. If extraneous or undesirable environmental noise is detected, the operator can immediately make another recording.

The circuit for transmitting the heart's trigger signal from the microphone 21 includes a source of electricity 37 and a passive, low-pass filter 38 designed to pass signals below 2,000 Hz. Any quality low-pass filter down to 50 Hz. would be suitable. The low-pass filter 38 includes a 3,900 ohm resistor 30b, and a 0.1 microfarad capacitor 32b. Each of these components has low-noise characteristics. From the low-pass filter 38, the trigger signal is transmitted to the tape recorder for recording on the second channel of the magnetic tape T.

During the monitoring of the sounds emanating from the patient's head, the patient's non-monitored eye is closed and the patient holds his breath for about 10 seconds, or for a length of time sufficient to record the sounds emanated from the patient's closed eye lid during 5 heartbeats. Subsequently, the microphone is moved to the patient's other eye lid and the procedure is repeated.

Figure 2:
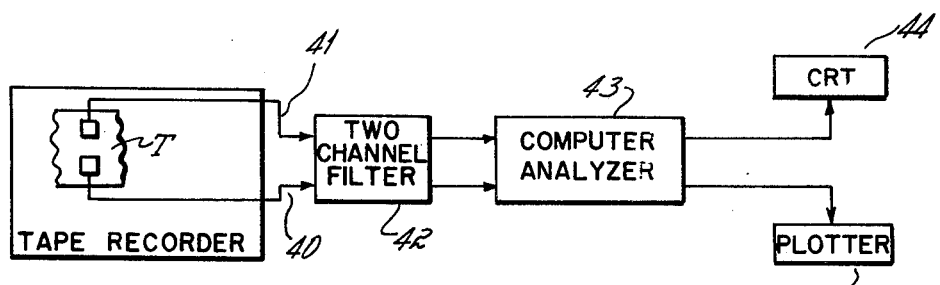
FIG. 2 is a diagrammatic illustration of the play-back, analysis portion of the invention.

Once the signals have been properly recorded on the magnetic tape, the taped signals can then be introduced to and analyzed by a computer/analyzer for the purpose of determining the probable existence of a cerebral aneurysm. The analyzing steps are diagrammatically shown in FIG. 2 wherein the signals from both channels of the tape are connected to a two channel variable filter 42. A variable filter manufactured by the Rockland Manufacturing Co. under its model designation No. 1042F has been found suitable. This two-channel filter 42 is set to pass trigger signals, indicated at 40, having a frequency of 50 Hz. and below, and to pass eye signals, indicated at 41, having a frequency of 800 Hz. and below. From the two-channel filter, both eye signal and trigger signal are connected to a computer/analyzer 43.

One specific computer/analyzer which has been found suitable is the Hewlett-Packard Fourier Analyzer Model No. 5451. This Hew-Packard system includes a means for subjecting the electrical signal produced by the eye lid sounds to Fourier analysis (Model 5451 Fourier Analyzer), a computer means (service computer Model 2100) for controlling the analysis and displaying its results, and a tape drive.

Fourier analysis of the eye signal provides and allows visualization of the signal (which is originally in the time domain) as a signal in the frequency domain. The analyzer provides a visual spectrum on the cathode-ray tube (CRT) 44 and a graphic plotter 45 is also connected to the analyzer for graphically plotting the spectrum displayed by the tube 44 for permanent record.

The visual display of Fourier analysis is analogous to the natural processing the ear and the brain performs on an acoustical signal. The ear allows interpretation of acoustical signals, not only in the dimensions of amptitude and duration, but also in the dimension of frequency; the Fourier analysis provides a visual display of this dimension of frequency.

Figure 4:
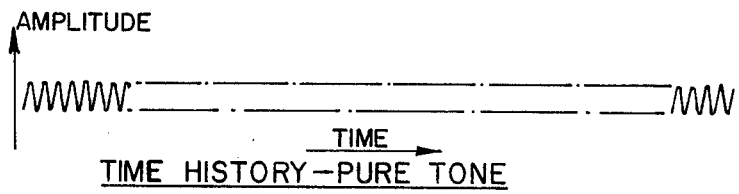
FIG. 4 is a plot of the time history of a pure tone.
Figure 5:
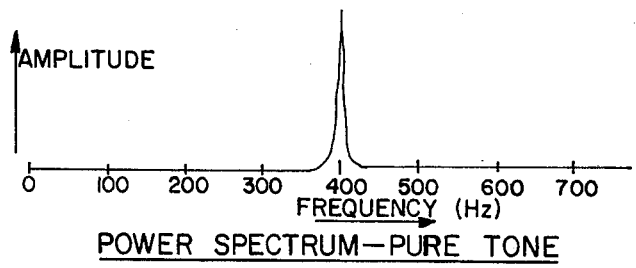
FIG. 5 is a plot of the frequency spectrum of a pure tone.
Figure 6:
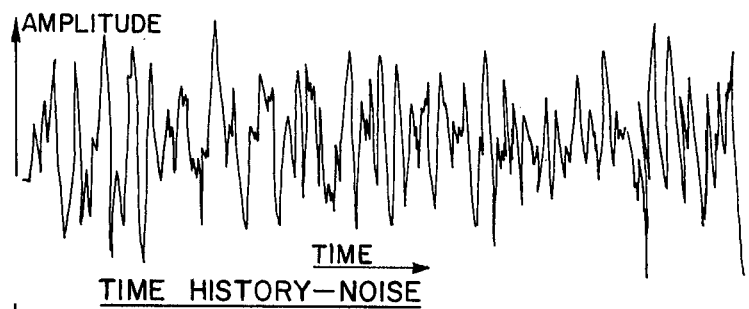
FIG. 6 is a plot of the time history of indiscriminate noise.
Figure 7:
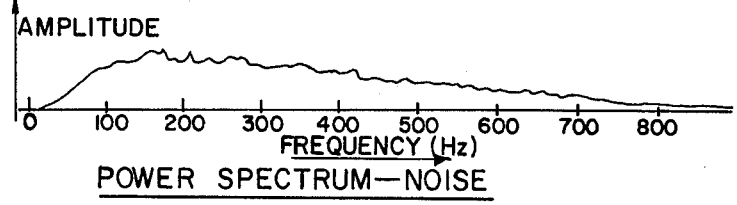
FIG. 7 is a plot of the frequency spectrum of indiscriminate noise.
Figure 8:
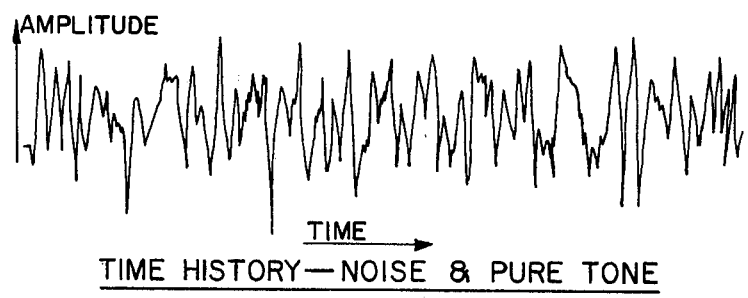
FIG. 8 is a plot of the time history of combined noise and pure tone.
Figure 9:
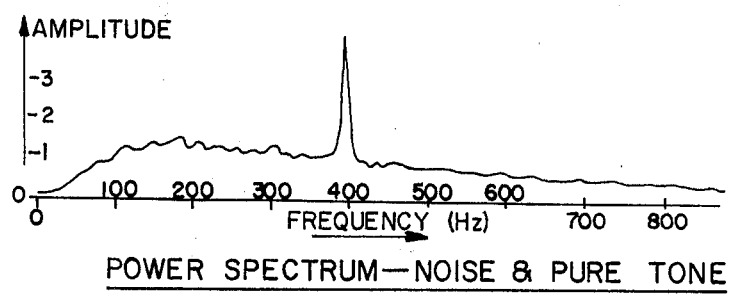
FIG. 9 is a plot of the frequency spectrum of combined noise and pure tone.

In the case of analysis of a pure tone, diagrammatically illustrated in FIG. 4, Fourier analysis produces a spectrum like that shown in FIG. 5, showing a single peak corresponding to the single tone the ear would hear. The time history of random noise, (heard as a deep tone pitch) shown in FIG. 6, produces a Fourier analysis spectrum like that shown in FIG. 7. The advantage of this analysis and display is that it overcomes the limitations of the ear alone. A pure tone, when combined with a noise signal, such as shown in FIG. 6, may not be seen in the time history such as shown in FIG. 8; however, the combination of a spectrum of a pure tone (FIG. 5) with the spectrum of noise (FIG. 7) produces a composite spectrum like that shown in FIG. 9, clearly showing the presence of the pure tone despite the noise.

COMPUTER SET-UP AND PROGRAM

The Hewlett-Packard computer is set up by connecting the trigger signal to the external trigger input provided on the computer, and by connecting the eye signal to the channel A input on the computer. The channel A overload of the computer is set at 4 volts; the trigger is set to give one trigger signal per heartbeat. The block size is set on the computer to 512 points and the frequency range of the computer is set from 0 to 1,000 Hz.

A computer program as follows is then loaded into the computer:

COMPUTER PROGRAM

| | | | |
|---|---|---|---|
| Program Initiation | 1 | Label | 0 |
| | 2 | Clear | 0 |
| | 3 | Clear | 1 |
| | 4 | Clear | 2 |
| Data Requisition | 5 | Label | 1 |
| | 6 | Analog | 0 1 |
| Data Manipulation | 7 | Clear | 0 0 50 |
| | 8 | Clear | 0 412 512 |
| | 9 | ← | 0 487 |
| Generation of Power-Spectrum Average | 10 | HAN | |
| | 11 | F | |
| | 12 | * | |
| | 13 | +1 | |
| | 14 | Store | 1 |
| | | Store | 2 |
| | 15 | Count | 1 5 |
| Data Normalization | 16 | f 2 | |
| | 17 | Clear | 2 0 255 |
| | 18 | ← | 2 255 |
| | 19 | f 2 | |
| | 20 | X1 | |
| | 21 | ÷2 | |
| Digital Filtering | 22 | Clear | 0 0 51 |
| | 23 | Clear | 0 205 256 |

Having passed the heart signal through the low-pass Rockland filter to eliminate the second heart sound, and the eye signal through the Rockland low-pass filter to prevent aliasing errors, the magnetic data tape is then started first to check the trigger and overload levels on the computer. The magnetic tape is then started, and when the operator hears the patient being told to hold his breath, the command jump o (go to label o) is made. The computer then initiates the program and holds at analog 0,1 until the trigger signal from the first heart sound is received. The computer then samples the data from the eye microphone during a predetermined brief pulse peak pressure at the cerebral vascular system and computes a spectrum. This process is repeated five times with each new spectrum added to the sum of the previous spectrums. When this procedure is completed, the composite spectrum is normalized in terms of total energy in the spectrums. The normalized spectrum is then digitally band/pass filtered between 200 Hz. and 800 Hz. to enhance the display which appears on the cathode-ray tube 44. The spectrum is then automatically plotted on graph paper by the plotter 45.

With respect to the monitoring sounds emanating from the patient's head and to the analysis and detection of an aneurysm-characteristic sound, the computer analysis of such sound is enhanced by analyzing data only when the tone generated by the aneurysm is normally present, such as for example, at a peak arterial pulse pressure moment. As can be appreciated from the above, the computer is programmed to sample data after a predetermined delay subsequent to the heartbeat trigger signal such that the data sampled by the computer corresponds to a period in time at which peak arterial pulse pressure is present in the cerebral vascular system. Further to enhance detection of an aneurysm-characteristic sound and to distinguish it from the other sounds monitored from the head, the date is averaged over approximately 5 cycles of peak arterial pulse pressure so that random signals or noise will tend to cancel out as displayed by the Fourier spectrum; the aneurysm tone will become more prominent.

DESCRIPTION OF EYE MICROPHONE ENCLOSURE

Figure 3:
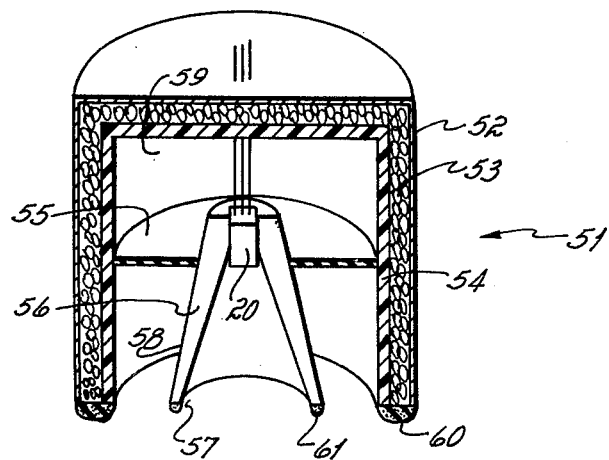
FIG. 3 is a cross-section diagrammatic illustration of one form of microphone monitor.

In order to isolate the aneurysm-characteristic sound wave desired to be monitored from ambient environmental or acoustical disturbance, the electronic microphone described above is enclosed in an acoustical isolation chamber which will now be described. An isolation chamber 51 is shown in FIG. 3 and is in the general form of a cylinder open at one end. The chamber includes an outer lead shell 52, an acoustical damping foam insulation 53 secured to the lead shell 52, and an inner plastic shell 54. A flat rubber supporting membrane 55 is attached to the inner plastic shell 54 and supports a funnel-like, porous, sound absorbing microphone support member 56 centrally in the chamber 51. The support 56 in turn surrounds and supports the microphone 20 and has an open lower end, as at 57, of approximately ½ inch in diameter. The support 56 is coated with a hard reflective coating on its external surface 58. The microphone 20 is connected, through appropriate leads extending through the upper end of the chamber 51, to the filtering and amplifying circuit as shown in FIG. 1. While the membrane 55 defines a damping chamber 59 in the upper end of the isolation chamber 51, the acoustical isolation of the chamber 51 may be filled with sound absorbent material other than air in order to provide further acoustical isolation for the microphone 20. The lower end of the isolation chamber 51 and of the absorbent support member 56 are provided with soft rubber sealing members 60 and 61. These serve respectively as air seals between the chamber 51 and the body structure surrounding the eye of the patient and in the case of seal 61 between the support member 56 and the closed eyelid of the patient. The flexible membrane movably supports the microphone support member so that it can be moved rearwardly when the cylinder is moved toward an eye and the support engages the eye lid before the cylinder is seated. This perfects an efficient seal of microphone and support to the eye lid and isolates the microphone from ambient noise.

Utilization of the acoustic isolation chamber 51 in combination with the microphone 20, as described, provides an acoustical pick-up means for effectively monitoring sound waves emanating from the eye of a patient and for initially converting the sound waves into an electronic signal which can be processed by the apparatus described above to indicate the probable existence of an intercranial aneurysm.

Of course, it should be appreciated that the amplitude of the aneurysm-characteristic sound waves emanating from the eye is extremely low. For that reason, it is important to minimize to a substantial degree any ambient environmental acoustical disturbance which could have a tendency to mask the sound wave generated by the aneurysm. While the microphone described above is effective to accomplish this objective, equivalent microphones and isolation means of other various constructions could be utilized.

It should also be appreciated that aneurysm-characteristic sound is emanated from the head in external areas other than the eye, and can be monitored over such other areas.

Further in this connection, it should be appreciated that it is possible to simultaneously monitor sound waves emanating from the head at different locations, and to analyze each of such sounds according to this invention. The signal from each microphone at each area is passed through a filter and amplifier circuit as shown in FIG. 1 and, each signal can be recorded on a separate channel on a multiple channel tape recorder. Each channel of the tape can be analyzed separately to determine the probable existence of intracranial aneurysms. The amplitude of a positive indication of an aneurysum-characteristic sound can be compared for each of the inputs to indicate the potential location of the aneurysm, for example, just as the amplitude of the spectrum peaks from each eye can be compared to indicate which side of the head the aneurysum is on as will be explained.

DIAGNOSTIC APPLICATION

Once the sound waves have been monitored and analyzed as described above, the graphic displays of the power spectrums can be analyzed to determine the probable existence of an aneurysm as well as to diagnosis and follow spasm. Of course, it would be possible to program a suitable computer to simply indicate whether or not the power spectrum indicated the probable existence of an aneurysm by analyzing the power spectrum and simply providing a yes or no signal by an appropriate indicator light, for example. However, the usefulness of the graphic display on the cathode-ray tube 44 or on the plotter 45 for diagnostic purposes can well be appreciated.

With respect to the displayed spectrum provided by the cathode-ray tube, the criteria established for the indication of the probable existence of an intracanial aneurysm is the presence of a single spike within the frequency range of 200 Hz. to 800 Hz. and having an amplitude about one and one-half times greater than any of the other spikes within a 50 Hz frequency of the spike in question. Thus, if a spike having these characteristics is present in the power spectrum, it is probable that a cerebral aneurysm exists.

In its simplest use, a pre-bleed patient is comfortably and inexpensively examined by the utilization of the invention described herein to determine the probable existence of a cerebral aneurysm. The actual test requires only about five minutes of the patient's time and can be performed in a doctors office or clinic, in the patient's home, or any other suitable location, the signals being recorded on the tape and then transmitted to a processing center for analysis. The procedure is appreciably less expensive than the only other current diagnostic technique, angiography, not to mention the fact that the present invention provides a risk-free method of detecting the probable existence of aneurysms as contrasted with the traumatic invasive technique of angiography. Should the method described herein indicate the probable existence of a cerebral aneurysm by displaying an aneurysm-characteristic spike, the patient can be treated accordingly, and preliminary to any bleed and spasm. Successful surgery at this stage is normally highly successful. The invention thus provides a means by which a patient may be easily and inexpensively examined for the possible presence of an aneurysm in the same instance where the gross technique of angiography might not have been indicated by the patient's symptoms.

In the event that a bleed has occurred, the invention described above is useful to determine the probable existence of an aneurysm prior to the onset of spasm. Once spasm occurs, however, it produces substantial masking noise which may render detection of the sound wave generated by the aneurysm improbable. Even at this stage, however, the invention described herein is very useful in order to follow vasospasm status of the patient. For example, spasm usually extends for a 1 to 2 week period. During that time, spasm generates sounds or bruits which are detectable by the invention. Such sounds or bruits are displayed on the cathode-ray tube 44 and the plotter 45 as peaks of wide band varying frequencies which tend to shift across the frequency band as indicated by spectrums generated by repeated data sampling during several days' time. (Spasm produces either a jet flow resulting in a wide band noise or a vortex shed resulting in a spectral display of a narrow band of spikes.) Such shifting of frequencies tends to indicate the existence of spasm and the changing condition of the patient's arteries.

Thus, the invention herein can be utilized to diagnose and follow the existence and cessation of spasm in a post-bleed aneurysm patient. Since the mortality and morbidity of surgery and risk of angiography is much higher with the presence of spasm, the invention is thus useful in indicating the existence of spasm by repeated sampling until spasm subsides. Angiography and surgery can then be delayed until that time when the risk of such is substantially reduced.

Even in those cases where a patient has arterial stenosis, which stenosis may generate sound waves or bruits due to the flow of blood in affected arteries, the invention herein is useful in differentiating spasm bruits therefrom by the expedient of serial monitoring. This is due to the fact that spasm usually develops on the third or fourth day after hemorrhage and usually disappears a few weeks later. Stenosis, however, does not normally present development and disappearance characteristics, and spasm can thus be differentiated therefrom despite the fact that spasm does not provide specific acoustic characteristics or features. Disappearance of spectral peaks one or two weeks post-bleed indicates the bruits were spasm-related while continuance of the peaks beyond this time indicates the bruits are stenosis related. Of course, serial monitoring made feasible by the invention is not possible or even desired with angiography due to its high risk during the presence of spasm, not to mention the expense and patient discomfort and trauma.

SAMPLE PATIENT DATA

In order to provide a still further understanding of the diagnostic uses of the invention, FIGS. 10–21a depict spectral displays produced as part of the history of the following patient examples. Several positive indications of aneurysms among the following examples were confirmed or preceeded by angiography, supporting the indications, made by the spectral display and the diagnosis based thereon. A number of patients described herein were monitored several times. Test results from recordings made at these various times were normally constant, further indicating the efficacy of the invention.

CONTROL PATIENT

To provide a control spectrum, sounds emanating from the left and right eyes of a patient having no known aneurysm were monitored and analyzed according to the invention. The spectral display obtained for each eye is depicted in FIGS. 10 and 10a. Both angiographic analysis and non-invasive analysis indicated a normal status.

PATIENT NO. 1

FIGS. 11 and 11a show spectral displays made from analysis of data taken over the left and right eyes of a 50-year old female who had fallen. Auditory monitoring alone detected no bruit, however, non-invasive monitoring and analysis of the sounds emanating from the right eye according to the invention indicated the probable existence of a cerebral aneurysm behind the right eye. Angiography demonstrated a large traumatic aneurysm of the right internal carotid artery in the siphon area. The peaks shown at about 200 Hz. in both spectrums are the results of eye blinking, hand movement or low frequency hum and are normally ignored. An extremely high amplitude at this frequency range, however, particularly when repeated for a number of samplings, may indicate the probable presence of an aneurysm as will be discussed with respect to Patient No. 7. They do not indicate aneurysm-characteristic sounds.

PATIENT NO. 2

A 37-year old male suffered sudden severe headache and blood was found in his cerebral spinal fluid. Angiography revealed an aneurysm in the anterior communicating artery behind the right eye. The aneurysm was successfully clipped and led to a full recovery. FIGS. 12 and 12a are pre-operative spectrums made from data monitored over the patient's respective left and right eyes; FIG. 12a indicates the probable existence of an aneurysm behind the right eye. No audible bruit was detected during the recording. Post-operative, non-invasive monitoring and analysis provided the spectrums of FIGS. 13 and 13a showing no aneurysm. This illustrates the effect of clipping the aneurysm and verifies that the aneurysm-characteristic peak of the pre-operative spike is the result of an aneurysm.

PATIENT NO. 3

This patient history depicts the usefulness of the invention described herein for the purpose of indicating the probable existence of aneurysm and for the purpose of following the vasospasm or stenosis status of the patient prior to and after various operative procedures relating to the cerebral vascular procedures performed on the patient. The 60-year old male patient was hospitalized for the investigation of transient strokes. The spectrum of the data recorded over the patient's right eye is shown in FIG.14a and shows a large bruit characterized by a plurality of relatively high amplitude spikes. The spectrum also shows a probable aneurysm-characteristic spike at approximately 600 Hz. The spectrum of the data recorded over the patient's left eye is shown in FIG. 14 and also shows a bruit and a large aneurysm spike. Preliminary angiography revealed approximately 90% stenosis of the siphon area on the right side and approximately 30% stenosis of the siphon area on the left side, thereby supporting the data spectrum of FIGS. 14 and 14a. An operation was performed on the patient to anastomose the right temporal artery to the right middle cerebral artery in order to provide more cerebral blood flow to the right hemisphere. The surgery was successful and the patient was released.

3 months later, the patient was again hospitalized with transient strokes. The spectrum of the data recorded over the right eye is shown in FIG. 15a and indicates a wide band bruit and an aneurysm spike at 600 Hz. The data recorded over the left eye also showed a large bruit and a possible aneurysm spike. The spectrum indications of the presence of an aneurysm and of stenosis-caused bruits was confirmed by angiography which showed approximately 90% stenosis of the right side area and approximately 80% stenosis of the left area. The aneurysm-characteristic spike produced from the data taken from the left eye was reduced in amplitude from the first recording (about three months earlier) and is apparently due to the bruits energy effecting the normalizing procedure of the sound wave analysis. Of course, the diagnosis of stenosis, as opposed to spasm is indicated by virtue of the fact that the peaks continued to exist beyond a 2-week period.

At this time, and in order to provide more cerebral blood flow to the left hemisphere, the left temporal artery was anastomosed to the left middle cerebral artery. After this operation, the data was re-recorded over both eyes and the spectrum resulting from such data is shown in FIGS. 16 and 16a. The spectrums show bruit energy from both eyes but the aneurysm spike has been eliminated. While the aneurysm spike is eliminated from the spectrum, (and without being preceeded by surgical clipping, etc.) it is not believed that the aneurysm has been eliminated, but rather that the change in blood flow, produced by the bypass surgical procedures, reduced or eliminated the vibration of the aneurysm so that a characteristic spike is not produced. The possibility of a false negative spectrum indicated will be hereinafter discussed.

From FIG. 14 through FIG. 16a and from the description of the patient's history, it can be appreciated that the invention herein is highly useful for following and diagnosing the vascular status of an aneurysm patient as one of ordinary skill in the art will be appreciated. It can be further appreciated that where there is substantial stenosis, invention herein is capable of distinguishing between the probable existence of an aneurysm and the existence of stenosis. Further, it will be noted that it is possible to utilize the present invention to follow the progression of stenosis. For example, contrasting FIGS. 14 and 15, it is seen that the stenosis increased substantially in the left siphon area over a three month period. Thus, repeated recordings and spectrums are useful not only in diagnosing the probable existence of aneurysm, but the progression of stenosis and the effect of operative procedures on stenosis and on stressed aneurysms.

PATIENT NO. 4

The spectrum of data recorded over the eyes of a 47-year old male is shown in FIGS. 17 and 17a, respectively. The spectrum in FIG. 17a shows an aneurysm spike as indicated. Angiography performed for other reasons revealed an incidental multilobulated anterior communicating aneurysm which was asymptomatic. Due to advanced atherosclerosis in the siphon area, the aneurysm spike is not as independent of other spikes as in other cases. However, it is of such magnitude as to be indicative of the probable existence of an aneurysm. Medical technology has reached the point where asymptomatic aneurysms of a certain size can be treated surgically to prevent a fatal accident or crippling stroke. The advantage of the invention in its ease of non-invasive screening of both symptomatic and asymptomatic patients is thus evident, as is its potential for following and noting changes in asymptomatic aneurysms (as opposed to angiography which does not lend itself to simple screening). Thus, the invention may provide a basis on which patients could be admitted to a hospital for angiography and elective surgery at a time when surgical risk is no more than an appendectomy, for example.

PATIENT NO. 5

False positive indications of the probable existence of an aneurysm by the invention herein have not been evidenced by conclusive facts to date. This patient history, however, illustrates the positive indication of a probable aneurysm by the invention wherein an angiogram did not evidence any aneurysm. The 62-year old female had a severe headache and was found to have blood in the cerebral fluid indicating a subarachnoid bleed. The spectrums of FIGS. 18 and 18a are of the data recorded over the patient's left and right eyes, respectively. The spectrum of FIG. 18 indicates a possible aneurysm spike as shown, together with wide band noise which can be associated with the expected spasm resulting from the aneurysm bleed. Thus, the spectrums of FIGS. 18 and 18a indicate vasospasm and a possible aneurysm over the left side. (It should be noticed that the possible aneurysm spike of FIG. 18 is of greater amplitude than the possible aneurysm spike of FIG. 18a, thereby indicating a left side aneurysm. In most aneurysm positive cases, as in this one, aneurysm spikes are produced in spectrums produced by both eye signals.) Angiography performed 2 days after the bleed indicated spasm but no aneurysm.

The spectrums of FIGS. 19 and 19a are of the data recorded over the patient's respective left and right eyes approximately 7 days post-bleed. These spectrums show a substantial clearing of the vaso-spasm and indicated the probable existence of an aneurysm over the left eye as shown in FIG. 19. Again, angiography at this time showed that the spasm had cleared and that there was a slight basilar artery dilation, but no definite aneurysm. Thus, there is no angiographic support in this patient history of the aneurysm-characteristic peak shown in the spectrums of FIGS. 18 through 19a.

There are several explanations for this and among these, two are believed most probable. The first is that the spasm itself could prevent the aneurysm from filling with enough contrast material, utilized in the angiographic technique, in order to show up on the arteriogram. Despite the fact that the spasm could prevent the aneurysm from filling with contrasting material, the aneurysm could still ring and produce a pure tone such as would produce a peak shown in the spectrums of FIGS. 18 through 19a. Another reason that the possible aneurysm was not positively indicated by the arteriogram is the possibility of a clot forming at the aneurysm such as would prevent the contrasting material of the angiogram technique from filling the aneurysm. The aneurysm could then still ring or produce the pure tone as would show up as a peak on the spectrum. Thus the facts of this patient history are not conclusive of a false positive indication of the possible existence of an aneurysm.

PATIENT NO. 6

A 34-year old male was admitted to the hospital emergency unit in a comatose state. He had previously been seen by a physician pursuant to complaints of headache. The spectrums of data recorded over the left and right eye, respectively, are shown in FIGS. 20 and 20a. Each spectrum included an aneurysm-characteristic spike as shown on the Figures and revealed adjacent peaks diagnosed as spasm. Since these spikes occurred in different spectrums, a diagnosis of two different aneurysms, one on each side, could be made. Angiography revealed spasm, an aneurysm on the anterior communicating carotid artery, and a suggestion of an aneurysm on the right carotid siphon area. This patient died, his comatose state not being suitable for performance of operative procedures. This exemplifies a situation where a patient exhibited simple headache not recognized as indicative of an aneurysm until it was too late to operate. The invention herein could eliminate such situations by early use.

PATIENT NO. 7

Patient No. 7 was a 23-year old female who entered the hospital's emergency unit on several occasions with severe headache. On the last entrance, the patient was awake and responsive but lapsed into coma moments after arrival. Data was recorded over both eyes and analyzed according to the invention to provide the spectrums of FIGS. 21 and 21a. The spectrums may be indicative of the probable existence of an aneurysm (spike at about 200 Hz.) particularly when the large peak is in the same frequency region as the spasm indicated by the multiple peaks of FIG. 21a, for example. Such a spectrum should be verified by several samplings, however, to negate the possibility of low frequency spike caused by blinking, movement, etc. Angiography was performed and supported the diagnosis of spasm and an anterior communicating aneurysm. This patient died within a few days after admission. Thus, this case history represents another situation where early use of the invention at a previous entrance could have indicated the aneurysm at a time when it was operable. This exemplifies the great need for the non-invasive method and apparatus of the invention herein which can be used easily and inexpensively on outpatients exhibiting simple headache, for example, where risky and expensive angiography would not be indicated.

OTHER PATIENT HISTORYS

Other patient historys indicate angiographically proven existence of aneurysm on the posterior communicating, middle cerebral, basilar, and posterior inferior cerebellar arteries where spectrums of the data recorded over the eyes of the patients did not clearly detect the probable existence of an aneurysm. Thus, it should be noted that while false positive indications have not been clearly evidenced to date, there is the possibility of false negative indications, i.e., no clear aneurysm spike shown in the spectrum where aneurysms are otherwise known to exist.

Explanations for the false negative diagnosis are several. For example, aneurysms on the rearward or posterior areas of the cerebral vascular system are substantially distally removed from the eyes as contrasted to aneurysm located on the anterior areas of the cerebral vascular system. This distance has a potentially critical damping effect upon the amplitude of the sound waves emanating from the aneurysms in the posterior area. Therefore, the sound may not be monitored, analyzed and produced as a high energy peak on the spectrum by the apparatus described herein, although more sensitive apparatus could be provided to efficiently monitor and analyze even these. Also, such damped aneurysm-created sound waves may be masked by coincidental spasm, other vascular bruits, or respirating sounds, for example.

Posterior aneurysms, however, are believed to comprise only about 15% of the total number of aneurysm. The majority of aneurysm are found in the anterior regions where the invention is most effective. Therefore, the small incidence of posterior aneurysm and the possible false negative indication does not significantly impare the usefulness of the invention.

Another possibility for a false negative indication would be in a post-operative status where a bypass procedure has been performed. This changes the characteristics of the blood flow in the aneurysm area such as would be sufficient to reduce or completely negate the sound wave production characteristics of the aneurysm.

It should be noted, however, that aneurysms in the posterior vascular regions more frequently produce aneurysm-characteristic symptoms than do aneurysms in the anterior regions. For example, posterior aneurysms may be likely to cause headache, dizziness, or fuzzy or double vision, in which case the skilled physician will be alerted to the fact that current techniques such as angiography might be indicated.

A further possible reason for false negative indications is the size of an aneurysm. Intracranial aneurysms exhibit more pronounced rupture tendencies when they reach a size approximately 5mm across. Smaller aneurysms may not separate an aneurysm characteristic sound monitorable by the equipment described herein. Thus, the possibility of false negatives are believed to have three explanations: 1) distal location, 2) smallness, and 3) masking. In the presence of aneurysm-symptoms, physicians will be alerted to the necessity of additional diagnostic techniques and the possibility of false negative indications does not impare the utility of the invention.

As previously stated, false positive indications have not to date been conclusively evidenced and thus have not impared the utility of the invention.

ADVANTAGES

It will thus be appreciated that the invention described herein provides an inexpensive, non-invasive technique for diagnosing the probable existence of cerebral aneurysms. As opposed to the expensive and traumatic angiography technique, the invention herein can be used easily and repeatedly in diagnosing the pre- and post-operative condition of the cerebral vascular system of a patient, and more particularly, to diagnose the onset of spasm and to follow the occurrence of spasm following an aneurysm bleed until the spasm ceases. In this manner, the invention is useful to indicate optimum times for the performance of angiography and of surgically corrective techniques. In addition, the invention is capable of displaying wide band bruits which are indicative of distinguishable stenosis or spasm. Even further, the invention can be used in following the progression of stenosis. Now, for the first time, the probable existence of cerebral aneurysms can be non-invasively detected and the physician can be supplied with a long needed tool having the potential of substantially reducing the incidence of death or brain damage due to intracranial aneurysm.

These and other advantages and modifications will become readily apparent to one of ordinary skill in the art without departing from the scope of the invention. For example, different spectrums may be used to aid diagnosis and treatment as will be readily appreciated by those of ordinary skill in the art. Also, different non-invasive monitoring means, analysis and indicating means can be utilized in place of the apparatus described in order to indicate the probable existence of an aneurysm via a self-contained portable unit. Still further, different, more sensitive apparatus could be utilized to detect the probable existence of aneurysms not typically indicated by the specific apparatus described above. The applicants therefore intend to be bound only by the claims appended hereto.

We claim:

1. A method for the non-invasive detection of the probable existence of intracranial aneurysms in humans comprising the steps of:
   monitoring sound waves emanating from an external predetermined area of the head,
   converting the monitored sound waves into an electrical signal, and
   analyzing the electrical signal to determine the existence of a sound having a constant frequency within the approximate range of 200 Hz. to 800 Hz., said constant frequency sound being indicative of the probable existence of an aneurysm.

2. A method as in claim 1 wherein said constant frequency sound is indicative of the probable existence of an aneurysm when said constant frequency sound has an amplitude about one and one-half times greater than the amplitude of any other monitored sound within 50 Hz. frequency of said constant frequency sound.

3. A method as in claim 1 including producing a power spectrum of said signal, said spectrum including an aneurysm-characteristic high energy peak when said constant frequency sound is detected.

4. A method as in claim 3 wherein said high energy peak is indicative of the probable existance of a cerebral aneurysm when said high energy peak has an amplitude about one and one-half times greater than any adjacent peak within 50 Hz. frequency of the frequency of said high energy peak.

5. A method as in claim 1 including sensing said sound waves over at least one eye.

6. A method as in claim 1 including electronically sensing said sound waves over a plurality of predetermined locations on the head.

7. A method as in claim 1 wherein a microphone is used to monitor sound waves and including the step of isolating monitored sound waves from environmental noise by acoustically blocking said environmental noise from said microphone.

8. A method as in claim 1 including the steps of:
filtering and amplifying said signals,
recording said signals,
analyzing said recorded signals and distinguishing constant frequency signals from their signals, and
graphically displaying the results of said analysis, said constant frequency signal being significantly displayed to indicate the probable existence of an intracranial aneurysm.

9. A method as in claim 1 including analyzing said signal at a time corresponding to peak arterial pulse pressure in the patient's head.

10. A method as in claim 1 including the steps of initiating said analysis in response to a trigger signal from a sound emanating from the heart and analyzing said signal after the generation of said heart sound at a time corresponding to peak arterial pulse pressure in the human head.

11. A method for non-invasively detecting the probable existence of intracranial aneurysms in human patients including the steps of:
monitoring sounds emanating from the patient's head,
analyzing said sounds by Fourier analysis to distribute the energy of the sounds in relation to frequency, said analysis generating a high energy signal in the presence of a constant frequency sound within the approximate range of 200 Hz. to 800 Hz., said constant frequency sound being indicative of the probable existence of an intracranial aneurysm, said high energy signal being indicative of the probable existence of an intracranial aneurysm when the signal has an amplitude about one and one-half times greater than the amplitude of any other generated signal within a frequency of 50 Hz.

12. A method for non-invasively detecting the probable existence of intracranial aneurysms in human patients including the steps of:
monitoring sounds emanating from patients' heads, and
analyzing said sounds to detect an aneurysm-characteristic sound.

13. A method as in claim 12 including the step of indicating the probable existence of an aneurysm when said aneurysm-characteristic sound is detected.

14. A method as in claim 12 including the step of analyzing said sounds at a time corresponding to peak arterial pulse pressure in the patient's head.

15. A method for non-invasively diagnosing the probable existence of an intracranial aneurysm in human patients and for non-invasively diagnosing the probable existence of spasm for the purpose of determining optimum low risk points in time for conducting angiography or surgical operative procedures including the steps of:
monitoring sound waves emanating from a patient's head, at a first time,
monitoring sound waves emanating from a patient's head at least a second time,
converting the monitored sound waves into electrical signals,
analyzing the signals to determine the existence of a body sound having a constant frequency within the approximate frequency range of 200 Hz. to 800 Hz. and the probable existence of an intracranial aneurysm when said constant frequency sound is found to exist for any monitored sound, and
analyzing the signals to determine the existence of other frequency sounds, the detection of a plurality of other frequency sounds within said approximate frequency range at one time and the absence or reduction of a plurality of other frequency sounds monitored at another time being indicative of the presence of spasm at said one time.

16. A method as in claim 15 including the steps of:
producing power spectrums of said signals, said spectrums including an aneurysm-characteristic high energy peak when said constant frequency sound is detected, and
said spectrums including a plurality of peaks of less energy amplitude in the presence of spasm.

17. A method as in claim 16 wherein said high energy peak is indicative of a cerebral aneurysm when it has an amplitude about one and one-half times greater than any adjacent peak within 50 Hz. frequency of the frequency of said high energy peak.

18. A method as in claim 16 including differentiating spasm from stenosis when each are capable of producing a plurality of said less-energy peaks in said spectrums by:
monitoring said sounds at different times to determine the existence or non-existence of said peaks of less energy in different spectrums, the presence of less energy peaks in one spectrum but not in another spectrum produced at a different time being indicative of the presence of spasm.

19. Apparatus for non-invasively detecting the probable existence of an intracranial aneurysm in human patients comprising:
means for monitoring sounds emanating from a patient's head, and
means for analyzing said sounds and for indicating the presence of an aneurysm-characteristic sound.

20. Apparatus as in claim 19 wherein said analyzing and indicating means include means for analyzing and indicating aneurysm-characteristic sounds having a constant frequency within the approximate frequency range of about 200 Hz. to 800 Hz. and an amplitude of about one and one-half times greater than other monitored sounds within 50 Hz. frequency of said aneurysm-characteristic sounds.

21. Apparatus as in claim 19 wherein said monitoring means includes:
an electronic microphone isolated from environmental noise,
a filter and amplifier circuit connected to said microphone for passing and amplifying signals in the frequency range between 150 Hz. to 2,000 Hz., and means for recording said filtered and amplified signals.

22. Apparatus as in claim 19 wherein said analyzing and indicating means includes a Fourier analyzer and a frequency spectrum display apparatus.

23. Apparatus as in claim 19 wherein said monitoring means includes a microphone system isolated from environmental noise, said system including:
- a cylinder defined by walls of a sound absorptive material and having an open end,
- a flexible membrane extending across said cylinder,
- a microphone support mounted in said membrane and spaced from said walls, and
- an electronic microphone supported in said support.

24. Apparatus as in claim 23 wherein a forward end of said microphone support extends forwardly of said membrane, said support being movable rearwardly into said chamber when said cylinder is moved toward an object which engages said support.

25. Apparatus as in claim 24 wherein said membrane defines an upper closed chamber in said cylinder and a lower open chamber in said cylinder.

26. Apparatus as in claim 23 wherein said cylinder walls are a composite including lead and foam.

* * * * *

UNITED STATES PATENT AND TRADEMARK OFFICE
CERTIFICATE OF CORRECTION

PATENT NO. : 4,008,711

DATED : February 22, 1977

INVENTOR(S) : Charles P. Olinger et al

It is certified that error appears in the above-identified patent and that said Letters Patent are hereby corrected as shown below:

Col. 1, line 31, "through" should be --though--.

Col. 1, line 53, "optimal condition" should be --optimal physical condition--.

Col. 2, line 22, delete "of".

Col. 2, line 43, "sound" should be --sounds--.

Col. 6, line 51, "Hew-Packard" should be --Hewlett-Packard--.

Col. 9, line 9, "emanting" should be --emanating--.

Col. 9, line 18, insert "or" between "ambient" and "environmental".

Col. 9, line 63, "intracanial" should be --intracranial--.

Col. 12, line 30, "3" should be -- Three --.

Col. 13, line 3, before "invention" insert -- the --.

UNITED STATES PATENT AND TRADEMARK OFFICE
CERTIFICATE OF CORRECTION

PATENT NO. : 4,008,711
DATED : February 22, 1977
INVENTOR(S) : Charles P. Olinger et al It is certified that error appears in the above–identified patent and that said Letters Patent are hereby corrected as shown below:

Col. 17, line 4, "existance" should be --existence--.

Col. 17, line 23, "their" should be --other--.

Signed and Sealed this

Sixth Day of December 1977

[SEAL]

Attest:

RUTH C. MASON
*Attesting Officer*

LUTRELLE F. PARKER
*Acting Commissioner of Patents and Trademarks*